United States Patent

Ishida et al.

[11] Patent Number: 5,817,427
[45] Date of Patent: Oct. 6, 1998

[54] TITANIUM OXIDE-CONTAINING PAPER, CORRUGATED BOARD, AND DEODORIZING ELEMENT

[75] Inventors: Tasaku Ishida, Moriyama; Hiroyasu Furukawa, Otsu; Seikichi Terawaki; Wataru Ohashi, both of Shiga, all of Japan

[73] Assignee: KG Pack Kabushiki Kaisha, Soka, Japan

[21] Appl. No.: 697,131

[22] Filed: Aug. 20, 1996

[30] Foreign Application Priority Data

Aug. 23, 1995 [JP] Japan .................................. 7-239308

[51] Int. Cl.$^6$ .............................. B32B 29/00; B32B 3/28; D21H 11/00
[52] U.S. Cl. ........................ 428/537.5; 428/182; 428/184; 428/328; 428/402; 428/702; 162/181.5; 55/521
[58] Field of Search ...................... 428/182, 184, 428/537.5, 326, 328, 402, 702; 162/109, 181.5; 55/521, 524; 131/202

[56] References Cited

U.S. PATENT DOCUMENTS 3,660,134  5/1972  Morris ................................. 106/308 Q
3,922,427  11/1975  Toyoda et al. ........................... 428/308
3,931,824  1/1976  Miano et al. ................................. 131/2
4,590,499  5/1986  Fujimura et al. ....................... 346/209

FOREIGN PATENT DOCUMENTS 1-111100  4/1989  Japan .

*Primary Examiner*—Donald Loney
*Attorney, Agent, or Firm*—Armstrong, Westerman, Hattori, McLeland & Naughton

[57] ABSTRACT

The invention has for its object to provide a titanium oxide-containing paper possessed of satisfactory deodorizing power and well protected against aging of paper, a corrugated board fabricated from the titanium oxide-containing paper, and a deodorizing element constructed using the corrugated board. The titanium oxide-containing paper comprises an ultrafine particulate titanium oxide with an X-ray particle diameter of not larger than 100 nm (T) or a modified ultrafine particulate titanium oxide available on surface-modification of (T) with a metal or a metal compound (T'), at least one inorganic filler (F) selected from the group consisting of sepiolite, silica gel, bentonite, zeolite, magnesium sulfate, asbestos, and active carbon for supporting the titanium oxide (T) or (T'), and an organic fiber material amenable to web formation by papermaking machine. The deodorizing element is constructed by stacking up a multiplicity of units of the above-mentioned corrugated board.

6 Claims, No Drawings

TITANIUM OXIDE-CONTAINING PAPER, CORRUGATED BOARD, AND DEODORIZING ELEMENT

FIELD OF THE INVENTION

The present invention relates to a titanium oxide-containing paper containing unmodified or surface-modified ultrafine titanium oxide particles. The invention further relates to a corrugated board comprising said titanium oxide-containing paper as at least one of its interliner and facing liner and to a deodorizing element comprising a stacked-up assembly of a multiplicity of units of said corrugated board.

BACKGROUND OF THE INVENTION

As a filter for removing odor components, contaminants and dust from an atmosphere, a deodorizing filter comprising a cartridge containing activated carbon in a nonwoven cloth or other fine-mesh housing adapted to be attached to an air conditioner has been employed.

Japanese Patent Kokai S59-69125 discloses an air-cleaning technology which comprises taking up a strip of creped or embossed paper in the form of a roll, with or without a deodorant or other chemical (e.g. activated carbon, deodorant, perfume, and/or desiccant) interposed between turns of the paper or incorporated in the paper, so that the air is cleaned as it flows from one end face of the roll to the other end face.

JP Kokai S56-15828, JP Kokai S56-16097, and JP Kokai S57-102221 disclose deodorizing elements such that for removal of malodors from an atmosphere, either one or both of a flat sheet material and a corrugated sheet material are constituted of an activated carbon fiber-containing paper and the two sheet materials are joined together.

Though not related to deodorization, JP Kokai S55-159827 discloses a dehumidifier for moisture-laden gases which is equipped with a built-in dehumidifying element comprising a honeycomb structure fabricated from an adsorbent (e.g. activated carbon)-containing paper and having a multiplicity of parallel gas channels and impregnated with a water absorbent (e.g. lithium chloride).

JP Kokai S62-114621, as filed by the present applicant, discloses a laminar structure for gas treatment which comprises a stacked-up assembly of a multiplicity of units of a corrugated board consisting of a flat ply sheet and a corrugated ply sheet and having a multiplicity of parallel channels, said ply sheets being made of a noncombustible paper which carries an extract or dry distillate of a plant of the family Theaceae.

Japanese Utility Model H4-106624, also filed by the present applicant, discloses a deodorizing filter comprising a honeycomb structure made up of a stack of many units of a corrugated board consisting of a flat ply sheet and a corrugated ply sheet and having a multiplicity of parallel channels so that a gas is cleaned as it flows through said parallel channels, characterized in that the deodorant chemical semicarbazide is deposited on said honeycomb structure.

Meanwhile, it has recently been reported that photocatalytic ultrafine particulate titanium oxide is effective in photodeodorization (removal of tobacco odor, household odor, body odor, etc.), cleaning of atmospheric air (removal of NOx, trichloroethane, etc.), decomposition of stains (tabacco tar, oil stain, etc.), protection against bacteria (sanitary porcelain, tiles), and improvement of water quality or cleaning of water. For detailed information, relevant descriptions in Denki Kagaku oyobi Kogyo Butsuri Kagaku (Electrochemistry and Industrial Physicochemistry), 68, No. 1, pp. 9–13, 1995, published by Shadan Hojin Denki Kagaku Kyokai (The Electrochemical Society of Japan) and Nikkei Business, Mar. 21, 1994 issue, pp. 60–61 are incorporated herein by reference.

There has also been reported a technology such that a titanium oxide sol prepared by aluminum hydroxide flocculation is added to an aqueous dispersion or slurry of wood pulp for use as a paper stock.

Among the above prior art technologies, said ultrafine particulate titanium oxide having photocatalytic activity is characterized in that it is activated by photic energy to oxidatively decompose many hazardous organic substances inclusive of malodorous substances and, as such, has the potential of being of use in the field of a deodorizing filter.

Therefore, the inventors of the present invention explored the possibility of incorporating ultrafine particulate titanium oxide in paper in the papermaking stage and using the resulting titanium oxide-containing paper for the fabrication of an air conditioner deodorizing element or as a wall paper having a deodorizing function. However, the inventors encountered the unexpected event that the incorporated ultrafine particulate titanium oxide decomposed not only malodorous substances but also oxidized and decomposed the matrix pulp in a short period of time. The investigation made by the inventors of the present invention revealed that apparently the pulp had been oxidatively decomposed at sites where it was in contact with particles of the titanium oxide.

Experiments were performed using an aluminum hydroxide-flocculated titanium oxide sol or a titanium oxide composition prepared by forced flocculation of an inorganic filler having a small adsorbent capacity and an ultrafine particulate titanium oxide with a flocculant as said ultrafine particulate titanium oxide. Although some improvements were obtained in the degradation of paper, many problems remained unsolved for commercial implementation.

Furthermore, the research done by the inventors of the present invention revealed that when applied to a deodorizing element adapted to be set on an air conditioner, the ordinary titanium oxide-containing paper merely containing ultrafine particulate titanium oxide has only a limited deodorizing effect and a need for further improvement was felt.

Developed in view of the above state of the art, the present invention has for its object to provide a titanium oxide-containing paper possessed of a satisfactory deodorizing power and well protected against paper degradation, a corrugated board comprising said titanium oxide-containing paper for at least one of its interliner and surfacing liner, a deodorizing element comprising a stack of a multiplicity of units of said corrugated board. The invention has for its further object to provide a modified ultrafine particulate titanium oxide-containing paper and the corresponding corrugated board and deodorizing element.

SUMMARY OF THE INVENTION

The titanium oxide-containing paper of the present invention is a paper essentially comprising an ultrafine particulate titanium oxide with a X-ray particle diameter of not larger than 100 nm (T) or a modified ultrafine particulate titanium oxide available on surface modification of (T) with a metal or a metal compound (T'), at least one inorganic filler (F) selected from the group consisting of sepiolite, silica gel, bentonite, zeolite, magnesium sulfate, asbestos, and activated carbon for supporting said ultrafine particulate titanium oxide (T) or modified ultrafine particulate titanium oxide (T'), and an organic fiber material (P) amenable to web formation by paper machine.

The corrugated board of the present invention comprises a wave-form interliner and a flat surfacing liner, with said titanium oxide-containing paper being used for said interliner or said flat liners or both.

The deodorizing element of the present invention comprises a stack of a multiplicity of units of said corrugated board.

DETAILED DESCRIPTION OF THE INVENTION

Titanium oxide-containing paper

As said ultrafine particulate titanium oxide (T), a product with an X-ray particle diameter (calculated by means of Scherrer's equation) of not larger than 100 nm is employed. The preferred X-ray diameter range is 2–50 nm and the still more preferred range is 3–30 nm. Such ultrafine grades of titanium oxide generally have photocatalytic activity. The crystal morphology of ultrafine particulate titanium oxide (T) is anatase in many cases but the rutile form can also be used. Such ultrafine particulate titanium oxide (T) is available in powdery form or in the form of a sol. Although the titanium oxide is generally used in powdery form (the BET surface area of the powder is $\geq 150$ m$^2$/g, preferably $\geq 180$ m$^2$/g, and for still better results, $\geq 200$ m$^2$/g), the sol can also be employed.

The above-mentioned ultrafine titanium oxide (T) can be used as it is for the purposes of the present invention. However, for a further improvement in deodorizing performance, the use of said modified ultrafine particulate titanium oxide (T') is preferred. The metal or metal compound that can be used for the surface modification of ultrafine particulate titanium oxide (T) includes various metals such as gold, silver, copper, platinum, zinc, silicon, iron, etc. and the oxides and hydroxides of such metals. The particularly preferred modifying agent is zinc oxide (or zinc oxide plus silicon oxide). The surface modification can be carried out in a variety of ways. Typically, the method described in JP Kokai H6-199524 can be utilized. Taking the surface modification with zinc oxide as an example, a typical procedure comprises mixing a dispersion of ultrafine particulate titanium oxide (T), a salt of zinc (e.g. zinc chloride, zinc sulfate, zinc nitrate, etc.) and an aqueous solution of an alkaline substance and neutralizing the mixture for precipitation, if necessary followed by rinsing and drying.

The weight ratio of the ultrafine particulate titanium oxide (T) to the modifying agent metal or metal compound in said modified ultrafine particulate titanium oxide (T') is selected from the range of generally 65:35 through 99:1, preferably 70:30 through 98:2, and for still better results, 75:25 through 97:3. If the proportion of the modifying agent is smaller than the above range, the degree of improvement in deodorizing effect will not be appreciable. On the other hand, if the proportion exceeds the above range, the deodorizing effect will be rather sacrificed.

The inorganic filler (F) is used to support said ultrafine particulate titanium oxide (T) or modified ultrafine particulate titanium oxide (T'). However, many ordinary inorganic fillers are widly divergent in adsorbency or immobilizing ability. In the practice of the present invention, at least one species selected from the group consisting of sepiolite, silica gel, bentonite, zeolite, magnesium sulfate, asbestos, and activated carbon is employed. Particularly preferred is sepiolite. By using such a specified filler, the relative amount of ultrafine particulate titanium oxide (T) or modified ultrafine particulate titanium oxide (T') in the paper sheet can be greatly increased. The inorganic filler (F) may be in any of the powdery, powder-like fibrous, and wisker forms.

The immobilizing capacity of said inorganic filler (F) for ultrafine particulate titanium oxide (T) or modified ultrafine particulate titanium oxide (T') can be estimated from the rate and state of flocculation of both kinds of particles in water. It can also be estimated by observing the paper web under the microscope at a magnification of about 1000–3000. The immobilizing capacity as the term is used herein means the intrinsic adsorbent-immobilizing power of the filler as such for ultrafine particulate titanium oxide (T) or modified ultrafine particulate titanium oxide (T'). Thus, if immobilization is achieved with the aid of a fixative of flocculating agent, the titanium oxide particles will be dislodged with time so that no satisfactory result will be obtained.

In this connection, ordinary inorganic materials such as aluminum hydroxide, kaolin, calcium, carbonate, and talc have only small adsorbent-immobilizing capacities for ultrafine particulate titanium oxide (T) or modified ultrafine particulate titanium oxide (T') and, though these materials can be concomitantly used, they cannot be sole substitutes for the inorganic filler (F) defined hereinbefore.

As the organic fiber material (P) amenable to web formation by papermaking machine, ordinary pulp can be used with advantage but other organic fiber materials can also be utilized only if they can be formed into a paper web.

In web formation, other reinforcing fibers such as glass fiber, ceramic fiber, and synthetic fiber can also be used in combination with said ultrafine particulate titanium oxide (T) or modified ultrafine particulate titanium oxide (T'), said inorganic filler (F), and organic fiber material (P). Organic or inorganic binders can also be added in suitable proportions. In addition, a variety of conventional papermaking auxiliary agents and additives can also be added.

The proportion of said ultrafine particulate titanium oxide (T) or modified ultrafine particulate titanium oxide (T') and said inorganic filler (F) combined with respect to the whole titanium oxide-containing paper should be generally 5–90 weight %, preferably 10–70 weight %, and for still better results, 20–60 weight %. The weight ratio of said ultrafine particulate titanium oxide (T) or modified ultrafine particulate titanium oxide (T') to said inorganic filler (F) should be 0.02–20, preferably 0.1–10, and for still better results, 0.5–5. The shortage of ultrafine particulate titanium oxide (T) or modified ultrafine particulate titanium oxide (T') results in a reduced deodorizing effect, while the excess titanium oxide leads to decreased paper strength. The shortage of said inorganic filler (F) results in a failure to adsorb and immobilize a necessary amount of said ultrafine particulate titanium oxide (T) or modified ultrafine particulate titanium oxide (T'). On the other hand, if the above-mentioned upper limit is exceeded, the resulting relative decrease in the amount of said ultrafine particulate titanium oxide (T) or modified ultrafine particulate titanium oxide (T') results in a shortage of deodorizing power.

The proportion of said organic fiber material (P) based on the whole paper should be generally 5–90 weight %, preferably 10–60 weight %, and for still better results, 10–40 weight %. The shortage of the organic fiber material (P) leads to insufficient paper strength, while an excess of (P) results in decreased relative amounts of ultrafine particulate titanium oxide (T) or modified ultrafine particulate titanium oxide (T') and inorganic filler (F), thus leading to a shortage of deodorizing power.

Papermaking can be carried out by dispersing said ultrafine particulate titanium oxide (T) or modified ultrafine particulate titanium oxide (T'), said inorganic filler (F), and said organic fiber material (P) (where necessary, reinforcing fiber, binder, auxiliary agents, additives, and other deodorant chemicals can also be added) in water and processing the dispersion into paper in accordance with the conventional wet process. In this manner, the desired titanium oxide-containing paper can be obtained.

The titanium oxide-containing paper thus obtained can be used for the production of a variety of paper products such as wall paper, sliding-door paper, calendar paper, packaging paper, printing paper, and handiwork paper.

Corrugated board

Using the above titanium oxide-containing paper, corrugated paper boards can be fabricated. As is well known, a corrugated board consists of a corrugated interliner and at least one flat facing liner. In accordance with the present invention, using said titanium oxide-containing paper for at least said interliner or said facing liner (preferably both), a corrugated board such as a single-faced board, a double-faced board, a double-wall, double-faced board, or a quadruple-wall, double-faced board is fabricated by means of a corrugator.

Deodorizing Element

By stacking up a multiplicity of units of the above corrugated board into an integral assembly (all tiers can be stacked in the same direction or, for the exchange of heat, stacked with each tier disposed at right angles with the adjacent tier), a honeycomb structure having a multiplicity of through-openings or channels can be obtained. This honeycomb structure can be used as a deodorizing element (filter) for a variety of appliances such as an air conditioner, an air cleaner, a dust collector, a deodorizer, a dehumidifier, and a blower or exhaust fan. This deodorizing element features a small pressure loss because of its inherent structure. When the honeycomb structure is fabricated with the constituent tiers being displaced stepwise, the light beam can be allowed to penetrate deeper into the structure in the irradiation step. The number of tiers of corrugated board and the height of each stage can be selected in consideration of filtration efficiency and pressure loss. When the element is applied to an air conditioner, for instance, the number of tiers is usually controlled to about 33–96/30 cm and the height of the tier to the range of 1.1–5.0 mm. The above deodorizing element may be provided with other chemicals and moisture conditioners.

In the titanium oxide-containing paper of the present invention, the inorganic filler (F) serves to effectively immobilize said ultrafine particulate titanium oxide (T) or modified ultrafine particulate titanium oxide (T') by way of adsorption. Under irradiation, the ultrafine particulate titanium oxide (T) or modified ultrafine particulate titanium oxide (T') exhibits a high oxidizing action to decompose the malodorous and organic substances in contact with the titanium oxide. Since the ultrafine particulate titanium oxide (T) or modified ultrafine particulate titanium oxide (T') is present as adsorbed and immobilized by the inorganic filler (F) within the paper, the area of contact between the ultrafine particulate titanium oxide (T) or modified ultrafine particulate titanium oxide (T') and the pulp or other organic fiber material (P) is very small so that even when the element is irradiated with light, the degradation of the paper is almost negligible despite the presence of the organic fiber material (P) which is organic by nature.

The modifying agent such as zinc oxide on the surface of modified ultrafine particulate titanium oxide (T') appears to adsorb and trap malodorous substances to assist in the oxidative decomposition of such substances by the ultrafine particulate titanium oxide (T). Therefore, only if the amount of surface modification by the modifying agent is proper, the modified ultrafine particulate titanium oxide (T') shows an increased deodorizing efficiency compared with the unmodified ultrafine particulate titanium dioxide (T).

With the titanium oxide-containing paper of the present invention, a remarkable deodorizing effect can be insured and, moreover, the malodorous substances such as hydrogen sulfide and ammonia which cannot be removed with the conventional adsorbent-type deodorizing system can be effectively eliminated. And as the titanium oxide-containing paper of the present invention is exposed to light during use or after use for deodorization, its deodorizing capacity is restored. Therefore, the paper can be used repeatedly. The deodorizing power of the titanium oxide-containing paper of the present invention is best exploited when it is processed into corrugated board and assembled into a deodorizing element.

Furthermore, the titanium oxide-containing paper of the present invention can be rendered flame-retardant or non-combustible by selecting suitable species of said component materials and their proportions.

The following examples are intended to illustrate the present invention in further detail and should by no means be construed as defining its scope. In the following examples, all "parts" are by weight.

Production of titanium oxide-containing paper

EXAMPLE 1

A titanium oxide-containing paper was manufactured by the usual wet papermaking method using 40 parts of photocatalytic titanium oxide ST-31 (crystal morphology: anatase, $TiO_2$ content after drying at 110° C.=81 wt. %, ZnO content 14 wt. %, X-ray particle dia. 7 nm, BET specific surface area 260 $m^2/g$) manufactured by Ishihara Sangyo Co. for modified ultrafine particulate titanium oxide (T'), 10 parts of sepiolite for in-organic filler (F), 20 parts of pulp for organic fiber material (P), 10 parts of ceramic fiber for reinforcing fiber, 10 parts of alumina sol binder, 5 parts of latex emulsion binder, and 5 parts of organic fibrous binder.

The resulting titanium oxide-containing paper weighed 161 $g/m^2$ and had a thickness of 0.26 mm, a density of 0.62 $g/cm^3$, and a tensile strength of 3.4 kg/15 mm. When this titanium oxide-containing paper was exposed to the fire of a cigaret lighter, it was non-combustible but was merely reduced in thickness without forming a char.

EXAMPLE 2

A titanium oxide-containing paper was manufactured by the usual wet papermaking method using 40 parts of photocatalytic titanium oxide ST-31 (crystal morphology: anatase, $TiO_2$ content after drying at 110° C.=95 wt. %, X-ray particle dia. 7 nm, BET specific surface area 320 $m^2/g$) manufactured by Ishihara Sangyo Co. for ultrafine particulate titanium oxide (T), 10 parts of sepiolite for inorganic filler (F), 20 parts of pulp for organic fiber material (P), 10 parts of ceramic fiber (the same as that used in Example 1), 10 parts of alumina sol binder, 5 parts of latex emulsion binder, and 5 parts of organic fibrous binder.

The resulting titanium oxide-containing paper weighed 160 $g/m^2$ and had a thickness of 0.25 mm, a density of 0.63 $g/cm^3$, and a tensile strength of 3.3 kg/15 mm. When this titanium oxide-containing paper was exposed to the fire of a cigaret lighter, it was non-combustible but was merely reduced in thickness without forming a char.

COMPARATIVE EXAMPLE 1

The procedure of Example 1 was repeated except that 10 parts of calcium carbonate was used in lieu of 10 parts of zeolite for inorganic filler (F). The resulting titanium oxide paper weighted 140 g/m² and had a thickness of 0.25 mm, a density of 0.56 g/cm³, and a tensile strength of 3.4 kg/15 mm. Because of the small adsorbent-immobilizing capacity of calcium carbonate, the modified ultrafine particulate titanium oxide (T') content was inevitably low as compared with Example 1.

COMPARATIVE EXAMPLE 2

Using an aggregate prepared from 40 parts of the same modified ultrafine particulate titanium oxide (T') as used in Example 1 and 10 parts of aluminum hydroxide as a filler with the aid of a flocculant and the same reinforcing fiber and binders as used in Example 1, a titanium dioxide-containing paper was manufactured in otherwise the same manner as Example 1. This titanium oxide-containing paper weighed 160 g/m² and had a thickness of 0.24 mm, a density of 0.67 g/cm³, and a tensile strength of 2.5 kg/15 mm.

COMPARATIVE EXAMPLE 3

Using an aggregate prepared from 40 parts of the same ultrafine particulate titanium oxide (T) as used in Example 2 and 10 parts of aluminum hydroxide as a filler with the aid of a flocculant and the same reinforcing fiber and binders as used in Example 2, a titanium oxide-containing paper was manufactured in otherwise the same manner as Example 2. This titanium oxide-containing paper weighed 162 g/m² and had a thickness of 0.25 mm, a density of 0.66 g/cm³, and a tensile strength of 2.6 kg/15 mm.

UV aging test

The titanium oxide-containing papers obtained in Examples 1 and 2 and Comparative Examples 1–3 were respectively irradiated with ultraviolet light with a 15 W UV fluorescent lamp from a height of 30 cm. The resulting changes in tensile strength and Hunter whiteness (JIS P8123) are shown below in Table 1. Comparison of Examples 1 and 2 with Comparative Examples 1–3 also indicate that the UV aging of the titanium oxide-containing papers of the present invention is within the tolerable range.

TABLE 1

|  | Example 1 | Example 2 | Comparative Example 1 | Comparative Example 2 | Comparative Example 3 |
| --- | --- | --- | --- | --- | --- |
| Before irradiation |  |  |  |  |  |
| Tensile strength (kg/15 mm) | 3.4 | 3.3 | 3.4 | 2.5 | 2.6 |
| Tensile strength retentivity (%) | 100 | 100 | 100 | 100 | 100 |
| Hunter whiteness (%) | 95.8 | 96.0 | 95.8 | 96.0 | 96.0 |
| After 10 days of irradiation |  |  |  |  |  |
| Tensile strength (kg/15 mm) | 3.0 | 2.7 | 2.5 | 2.0 | 2.0 |
| Tensile strength retentivity (%) | 88 | 82 | 74 | 80 | 77 |
| Hunter whiteness (%) | 95.4 | 95.4 | 95.4 | 95.6 | 95.6 |
| After 20 days of irradiation |  |  |  |  |  |
| Tensile strength (kg/15 mm) | 2.8 | 2.6 | 1.7 | 1.6 | 1.6 |
| Tensile strength | 82 | 79 | 50 | 64 | 62 |

TABLE 1-continued

|  | Example 1 | Example 2 | Comparative Example 1 | Comparative Example 2 | Comparative Example 3 |
| --- | --- | --- | --- | --- | --- |
| retentivity (%) |  |  |  |  |  |
| Hunter whiteness (%) | 95.2 | 95.2 | 95.2 | 95.4 | 95.2 |
| After 30 days of irradiation |  |  |  |  |  |
| Tensile strength (kg/15 mm) | 2.7 | 2.4 | 1.1 | 1.2 | 1.2 |
| Tensile strength retentivity (%) | 79 | 73 | 32 | 48 | 46 |
| Hunter whiteness (%) | 95.1 | 95.0 | 95.0 | 95.2 | 95.0 |

Evaluation of the deodorizing efficiency of titanium oxide-containing paper

A testpiece, sized 0.01 m², of the titanium oxide-containing paper obtained in Example 1 or of the paper obtained in Example 2 and malodorous substances (ammonia, $NH_3$; acetic acid, $CH_3COOH$; hydrogen sulfide, $H_2S$) were placed together in a sealed 5-L glass bottle and a 4-W UV fluorescent lamp was positioned at an irradiation distance with respect to the testpiece. The bottle was left standing at room temperature for 1 hour and the residual gas concentrations were measured with gas sensor tubes. As control, a blank experiment was carried out without placing the titanium oxide-containing paper in the bottle. The results of the experiment using the paper of Example 1 are presented in Table 2 and the results obtained with the paper of Example 2 are presented in Table 3.

TABLE 2

| Malodorous substance | $TiO_2$-containing paper | UV irradiation | Concentration after 1 hr | % Removal |
| --- | --- | --- | --- | --- |
| $NH_3$ | Absent | Absent | 1700 ppm | — |
| $NH_3$ | Present | Absent | 320 ppm | 82.4% |
| $NH_3$ | Present | Present | 180 ppm | 89.6% |
| $CH_3COOH$ | Absent | Absent | 300 ppm | — |
| $CH_3COOH$ | Present | Absent | 60 ppm | 80.0% |
| $CH_3COOH$ | Present | Present | 10 ppm | 96.7% |
| $H_2S$ | Absent | Absent | 1100 ppm | — |
| $H_2S$ | Present | Absent | 20 ppm | 98.2% |
| $H_2S$ | Present | Present | 10 ppm | 99.1% |

TABLE 3

| Malodorous substance | $TiO_2$-containing paper | UV irradiation | Concentration after 1 hr | % Removal |
| --- | --- | --- | --- | --- |
| $NH_3$ | Absent | Absent | 1680 ppm | — |
| $NH_3$ | Present | Absent | 420 ppm | 75.0% |
| $NH_3$ | Present | Present | 240 ppm | 85.7% |
| $CH_3COOH$ | Absent | Absent | 280 ppm | — |
| $CH_3COOH$ | Present | Absent | 80 ppm | 71.4% |
| $CH_3COOH$ | Present | Present | 20 ppm | 92.9% |
| $H_2S$ | Absent | Absent | 1000 ppm | — |
| $H_2S$ | Present | Absent | 30 ppm | 97.0% |
| $H_2S$ | Present | Present | 20 ppm | 98.0% |

It will be apparent from Tables 2 and 3 that the titanium oxide-containing papers of the present invention have very satisfactory deodorizing capacities and exhibit further improved deodorizing performances when UV irradiation is concomitantly carried out. Production of titanium oxide-containing paper

EXAMPLE 3

A titanium oxide-containing paper was manufactured by the usual wet papermaking method using 30 parts of the same modified ultrafine particulate titanium oxide as used in Example 1, 7 parts of zeolite for inorganic filler (F), 20 parts of activated carbon with a particle size of 10 and odd $\mu$m, 20 parts of pulp for organic fiber material (P), 8 parts of ceramic fiber for said reinforcing fiber, 5 parts of alumina sol binder, 6 parts of latex emulsion binder, and 4 parts of organic fibrous binder. The resulting titanium oxide-containing paper weighed 171 g/m$^2$ and had a thickness of 0.29 mm, a density of 0.59 g/cm$^3$, and a tensile strength of 2.7 kg/15 mm.

A titanium oxide-containing paper was manufactured by the usual wet papermaking method using 30 parts of the same ultrafine particulate titanium oxide (T) as used in Example 2, 7 parts of zeolite for inorganic filler (F), 20 parts of activated carbon with a particle size of 10 and odd $\mu$m, 20 parts of pulp for organic fiber material (P), 8 parts of ceramic fiber for said reinforcing fiber, 5 parts of alumina sol binder, 6 parts of latex emulsion binder, and 4 parts of organic fibrous binder. The resulting titanium oxide-containing paper weighed 170 g/m$^2$ and had a thickness of 0.28 mm, a density of 0.61 g/cm$^3$, and a tensile strength of 2.8 kg/15 mm.

Construction of a deodorizing element

Each of the titanium oxide-containing papers obtained in Example 3 and 4 was fed to a corrugator to fabricate a one-faced corrugated board consisting of a wave-form interliner and a flat surfacing liner. This one-faced corrugated board was cut to 15 mm×300 mm and the resulting units were stacked up into a 50-tier assembly. The assembly was placed in an aluminum frame and revetted to provide a deodorizing element.

Determination of deodorizing efficacy

The above deodorizing element was set on a household air cleaner and the deodorizing efficacy against the tobacco-derived ammonia, acetaldehyde, acetic acid, and hydrogen sulfide was evaluated by the following procedure.

(1) A 1 m$^3$ (1 m×1 m×1 m) glass testing box equipped with an agitation fan, windows adapted to open and close and communicating with an air cleaner and a tobacco smoking machine, and an insertion hole for sensor tubes was provided. In consideration of the volume of a standard Japanese room (24 m$^3$), natural ventilation coefficient, tobacco length ratio, wall adsorption rate, and the difference between human smoking and mechanical smoking, the above testing box was equivalent to about 1/40 of said standard room.

(2) With the operation of the air cleaner stopped, 5 cigarets (the brand Mild Seven) were set on the tobacco smoking machine fitted with a disk-shaped tobacco holder behind a blower and with the agitation fan being driven at 0.5 m$^3$/min., the 5 cigarets were concurrently combusted over 5–7 minutes. In this experiment, the operation of the tobacco smoking machine was stopped when the cigaret combusting at the highest rate had burned down to the tobacco filter and the remaining cigarets were allowed to combust spontaneously.

(3) Two to 5 minutes after completion of combustion of the cigarets, the initial concentrations of malodorous components were measured with detection tubes. In this connection, an ammonia sensor tube and an acetaldehyde sensor tube were connected in series to measure the concentrations of ammonia and acetaldehyde simultaneously. Then, the concentration of acetic acid was measured with an acetic acid sensor tube.

(4) After determination of initial concentrations, the air cleaner was operated for 30 minutes and, then, stopped. The concentrations of the malodorous substances were measured again in the same manner as above.

(5) To evaluate the useful life of the element set on the air cleaner, the above procedures (2), (3), and (4) were repeated.

The results with the paper of Example 3 and the paper of Example 4 are shown in Table 4 and 5, respectively. In the tables, "n" means the number (cumulative number) of cigarets. "Initial/30" means the initial concentration (ppm)/concentration (ppm) after 30 min. operation of the air cleaner. "% Removal" means the percent removal rate. "–" represents no determination.

TABLE 4

| | | $NH_3$ | | $CH_3CHO$ | | $CH_3COOH$ | | $H_2S$ | |
|---|---|---|---|---|---|---|---|---|---|
| Run | n | Initial/30 | % Removal | Initial/30 | % Removal | Initial/30 | % Removal | Initial/30 | % Removal |
| 1 | 5 | 25/1 | 96.0 | 12/1 | 91.7 | 10/0 | 100.0 | 35/0 | 100.0 |
| 2 | 10 | 22/2 | 90.9 | 13/2 | 84.6 | 13/1 | 92.3 | 35/0 | 100.0 |
| 3 | 15 | 30/4 | 86.7 | 10/2 | 80.0 | 10/1 | 90.0 | 35/0 | 100.0 |
| 4 | 20 | 27/5 | 81.5 | 10/2 | 80.0 | 12/1 | 91.7 | 35/0 | 100.0 |
| 5 | 25 | 30/7 | 76.7 | 11/3 | 72.7 | 10/2 | 80.0 | 35/0 | 100.0 |
| 6 | 30 | 25/9 | 64.0 | 12/5 | 58.3 | 12/2 | 83.3 | — | — |
| 7 | 35 | 30/10 | 66.7 | 12/7 | 41.7 | 10/2 | 80.0 | — | — |
| 8 | 40 | 34/14 | 58.8 | 10/8 | 20.0 | 14/3 | 78.6 | — | — |
| 9 | 45 | 27/18 | 33.3 | — | — | 11/3 | 72.7 | — | — |
| 10 | 50 | 35/20 | 42.9 | — | — | 12/3 | 75.0 | — | — |
| 15 | 75 | — | — | — | — | 13/4 | 69.2 | — | — |
| 20 | 100 | — | — | — | — | 10/5 | 50.0 | — | — |
| 25 | 125 | — | — | — | — | 10/6 | 40.0 | — | — |

TABLE 5

| $NH_3$ | $CH_3CHO$ | $CH_3COOH$ | $H_2S$ |
|---|---|---|---|

| Run | n | Initial/30 | % Removal | Initial/30 | % Removal | Initial/30 | % Removal | Initial/30 | % Removal |
|---|---|---|---|---|---|---|---|---|---|
| 1 | 5 | 20/1 | 95.0 | 13/1 | 92.3 | 12/0 | 100.0 | 35/0 | 100.0 |
| 2 | 10 | 25/2 | 92.0 | 12/2 | 83.3 | 10/1 | 90.0 | 35/0 | 100.0 |
| 3 | 15 | 23/4 | 82.6 | 12/3 | 75.0 | 12/1 | 91.7 | 35/0 | 100.0 |
| 4 | 20 | 30/7 | 76.7 | 11/4 | 63.6 | 10/1 | 90.0 | 35/0 | 100.0 |
| 5 | 25 | 25/9 | 64.0 | 11/5 | 54.5 | 13/2 | 84.6 | 35/0 | 100.0 |
| 6 | 30 | 24/11 | 54.2 | 10/6 | 40.0 | 10/2 | 80.0 | — | — |
| 7 | 35 | 25/12 | 52.0 | 12/8 | 33.3 | 12/2 | 83.3 | — | — |
| 8 | 40 | 22/13 | 40.9 | — | — | 11/3 | 72.7 | — | — |
| 9 | 45 | 25/16 | 36.0 | — | — | 13/3 | 76.9 | — | — |
| 10 | 50 | — | — | — | — | 13/4 | 69.2 | — | — |
| 15 | 75 | — | — | — | — | 12/5 | 58.3 | — | — |
| 18 | 90 | — | — | — | — | 13/6 | 53.8 | — | — |
| 20 | 100 | — | — | — | — | 12/7 | 41.7 | — | — |

It is apparent from Tables 4 for Example 3 that the cumulative number of cigarets till the % removal value had dropped to ≦50% was 40 for ammonia, 30 for acetaldehyde, and 100 for acetic acid, indicating that the invention is effective in the elimination of malodorous substances, particularly hydrogen sulfide. It is also apparent from Table 5 for Example 4 that the paper of Example 4 is nearly effective as the paper of Example 3 in the elimination of malodorous substances.

Construction of a deodorizing element

Each of the titanium oxide-containing papers obtained in Examples 3 and 4 was fed to a corrugator to fabricate a single-faced corrugated board consisting of a wave-form interliner and a flat liner. This corrugated board was cut to 5 mm×100 mm and the resulting units were stacked up in 11 tiers to provide a deodorizing element.

Determination of static deodorizing power

The deodorizing element obtained above and malodorous substances (ammonia, $NH_3$; acetaldehyde, $CH_3CHO$, acetic acid, $CH_3COOH$) were placed in a 5-L glass bottle, with a 4-W UV fluorescent lamp being fixed in a position capable of irradiating said deodorizing element, and the bottle was allowed to sit at room temperature for a predetermined time (1 hr or 6 hrs). Then, the residual gas concentrations were measured with gas sensor tubes. As control, a blank experiment was performed without placing the deodorizing element in the bottle. The results for Example 3 and Example 4 are shown in Tables 6 and 7, respectively.

TABLE 6

| Malodorous substance | Element | UV irradiation | Concentration after 1 hr (ppm)/% removal | Concentration after 6 hr (ppm)/% removal |
|---|---|---|---|---|
| $NH_3$ | Absent | Absent | 1600/— | 1560/— |
| $NH_3$ | Present | Absent | 400/75.0 | 360/76.9 |
| $NH_3$ | Present | Present | 220/86.3 | 15/99.0 |
| $CH_3CHO$ | Absent | Absent | 800/— | 800/— |
| $CH_3CHO$ | Present | Absent | 300/62.5 | 240/70.0 |
| $CH_3CHO$ | Present | Present | 80/90.0 | 0/100.0 |
| $CH_3COOH$ | Absent | Absent | 380/— | 390/— |
| $CH_3COOH$ | Present | Absent | 25/93.4 | 15/96.2 |
| $CH_3COOH$ | Present | Present | 10/97.4 | 3/99.2 |

TABLE 7

| Malodorous substance | Element | UV irradiation | Concentration after 1 hr (ppm)/% removal | Concentration after 6 hr (ppm)/% removal |
|---|---|---|---|---|
| $NH_3$ | Absent | Absent | 1600/— | 1560/— |
| $NH_3$ | Present | Absent | 500/68.8 | 400/74.4 |

TABLE 7-continued

| Malodorous substance | Element | UV irradiation | Concentration after 1 hr (ppm)/% removal | Concentration after 6 hr (ppm)/% removal |
|---|---|---|---|---|
| $NH_3$ | Present | Present | 380/76.3 | 25/98.4 |
| $CH_3CHO$ | Absent | Absent | 800/— | 800/— |
| $CH_3CHO$ | Present | Absent | 340/57.5 | 300/62.5 |
| $CH_3CHO$ | Present | Present | 120/85.0 | 10/98.8 |
| $CH_3COOH$ | Absent | Absent | 380/— | 390/— |
| $CH_3COOH$ | Present | Absent | 40/89.5 | 20/94.9 |
| $CH_3COOH$ | Present | Present | 20/94.7 | 5/98.7 |

It will be apparent from Tables 6 and 7 that the titanium oxide-containing papers of the present invention have excellent deodorizing capacities and exhibit still improved deodorizing performances when UV irradiation is concomitantly applied.

EXAMPLES 5–8

The procedure of Example 1 was repeated except that 10 parts of silica gel (Example 5), 10 parts of bentonite (Example 6), 10 parts of magnesium sulfate (Example 7), or 2 parts of zeolite plus 8 parts of asbestos (Example 8) was used in lieu of 10 parts of sepiolite.

Each of the above titanium oxide-containing papers was irradiated with UV light with a 15-W UV fluorescent lamp from a height of 30 cm to evaluate the aging resistance of the paper. The tensile strength retentivity after 30 days of exposure was 77%, 78%, 75%, and 79% for Examples 5–8.

Testpieces, each sized 0.01 $m^2$, of the respective titanium oxide-containing papers were irradiated with a 4-W UV fluorescent lamp in the same manner as Example 1 and the percent removal rates were determined. The % removal rates after one-hour standing for Examples 5, 6, 7, and 8 were 88.6%, 86.5%, 88.2%, and 87.8%, respectively, for ammonia, 96.1%, 94.7%, 93.4%, and 95.9%, respectively, for acetic acid, and 98.5%, 95.8%, 97.7%, and 98.2%, respectively, for hydrogen sulfide.

In the titanium oxide-containing paper of the present invention, the ultrafine particulate titanium oxide (T) or modified ultrafine particulate titanium oxide (T') is present as adsorbed and immobilized by the inorganic filler (F) within the paper, so that the area of contact between the ultrafine particulate titanium oxide (T) or modified ultrafine particulate titanium oxide (T') and the pulp or other organic fiber material (P) is very small so that even when the element is irradiated with light, the degradation of the paper is almost negligible despite the presence of the organic fiber material (P) which is organic by nature.

Under light, the ultrafine particulate titanium oxide (T) or modified ultrafine particulate titanium oxide (T') adsorbed and immobilized by the inorganic filler (F) exhibits a high oxidizing action to decompose the malodorous and organic substances in contact with the titanium oxide. A remarkable deodorizing effect can be obtained (particularly when the modified ultrafine particulate titanium oxide was used) and, moreover, the malodorous substances such as hydrogen sulfide and ammonia which cannot be removed with the conventional adsorbent-type deodorizing system can be effectively eliminated. And as the titanium oxide-containing paper of the present invention is exposed to light during use or after use for deodorization, its deodorizing capacity is restored. Therefore, the paper can be used repeatedly. The deodorizing power of the titanium oxide-containing paper of the present invention is best exploited when it is processed into corrugated board and assembled into a deodorizing element.

Thus, the corrugated board fabricated from the titanium oxide-containing paper of the present invention and the deodorizing element constructed by stacking up a plurality of units of said corrugated board are of great practical value.

What is claimed is:

1. A titanium oxide-containing paper comprising a blend of an ultrafine particulate titanium oxide with an X-ray particle diameter of 2–50 nm (T) or titanium oxide with an X-ray particle diameter of 2–50 nm which surface has been treated by reaction with a metal or metal compound (T'), at least one inorganic filler (F) selected from the group consisting of sepiolite, silica gel, bentonite, zeolite, magnesium sulfate, asbestos, and active carbon for supporting said titanium oxide (T) or (T'), and an organic fiber material (P) amenable to web formation by papermaking machine, wherein the combined amount of said titanium oxide (T) or (T') and said inorganic filler (F) is equal to 5–90 weight % based on the whole titanium oxide-containing paper, the weight ratio of said titanium oxide (T) or (T') to said inorganic filler (F) is 0.02–20, and the proportion of said organic fiber material is 5–90 weight %.

2. The titanium oxide-containing paper of claim 1 wherein the weight ratio of said ultrafine particulate titanium oxide (T) to said metal or metal compound modifying the surface of (T) in said modified ultrafine particulate titanium oxide (T') is 65:35 through 99:1.

3. A corrugated board comprising a wave-form interliner and at least one flat facing liner, wherein the titanium oxide-containing paper claimed in claim 1 is used for at least one of said interliner and flat facing liner.

4. A deodorizing element comprising a stacked-up assembly of a multiplicity of units of the corrugated board claimed in claim 3.

5. A corrugated board comprising a wave-form interliner and at least one flat facing liner, wherein the titanium oxide-containing paper claimed in claim 2 is used for at least one of said interliner and flat facing liner.

6. A deodorizing element comprising a stacked-up assembly of a multiplicity of units of the corrugated board claimed in claim 5.

* * * * *